(12) United States Patent
Higuchi et al.

(10) Patent No.: US 7,608,456 B2
(45) Date of Patent: Oct. 27, 2009

(54) MICRO PLATE TREATING DEVICE AND MICRO PLATE CARRYING METHOD

(75) Inventors: Akira Higuchi, Fukuoka (JP); Eiji Watanabe, Fukuoka (JP)

(73) Assignee: Panasonic Corporation, Osaka (JP)

( * ) Notice: Subject to any disclaimer, the term of this patent is extended or adjusted under 35 U.S.C. 154(b) by 357 days.

(21) Appl. No.: 10/554,924

(22) PCT Filed: Apr. 5, 2005

(86) PCT No.: PCT/JP2005/006986

§ 371 (c)(1),
(2), (4) Date: Oct. 31, 2005

(87) PCT Pub. No.: WO2005/098453

PCT Pub. Date: Oct. 20, 2005

(65) Prior Publication Data

US 2006/0210431 A1  Sep. 21, 2006

(30) Foreign Application Priority Data

Apr. 7, 2004  (JP)  ............................. 2004-112975

(51) Int. Cl.
  *G01N 35/02* (2006.01)
  *G01N 35/04* (2006.01)
(52) U.S. Cl. .................... 436/48; 436/43; 436/47; 436/49; 422/63; 422/65; 422/100; 141/129; 141/130
(58) Field of Classification Search .................. None
  See application file for complete search history.

(56) References Cited

U.S. PATENT DOCUMENTS

| 3,844,896 | A | * | 10/1974 | Sharpe | 435/286.4 |
| 5,985,214 | A | * | 11/1999 | Stylli et al. | 422/65 |
| 6,360,792 | B1 | * | 3/2002 | Ganz et al. | 141/129 |
| 6,979,425 | B1 | * | 12/2005 | Ganz et al. | 422/100 |
| 2002/0119077 | A1 | * | 8/2002 | Shumate et al. | 422/100 |
| 2003/0044991 | A1 | * | 3/2003 | Haslam et al. | 436/47 |

FOREIGN PATENT DOCUMENTS

| JP | 11-223636 A | 8/1999 |
| JP | 2002-340912 A | 11/2001 |
| JP | 2004-85521 A | 3/2004 |

* cited by examiner

*Primary Examiner*—P. Kathryn Wright
(74) *Attorney, Agent, or Firm*—McDermott Will & Emery LLP

(57) ABSTRACT

In a microplate processing apparatus that removes lid (11) of microplate (10) conveyed by microplate conveying mechanism (3), performs a dispensing process by dispensing head (8), and attaches lid (11) after the dispensing process is completed, lid (11) removed by lid removing mechanism (6) at second position (P2), is conveyed to fourth position (P4) located downstream, in advance of microplate (10) with this lid (11) having been attached, by microplate conveying mechanism (3), to be retained by lid attaching mechanism (9), and then is attached to microplate (10) having been conveyed to fourth position (P4), after the dispensing process is completed.

2 Claims, 6 Drawing Sheets

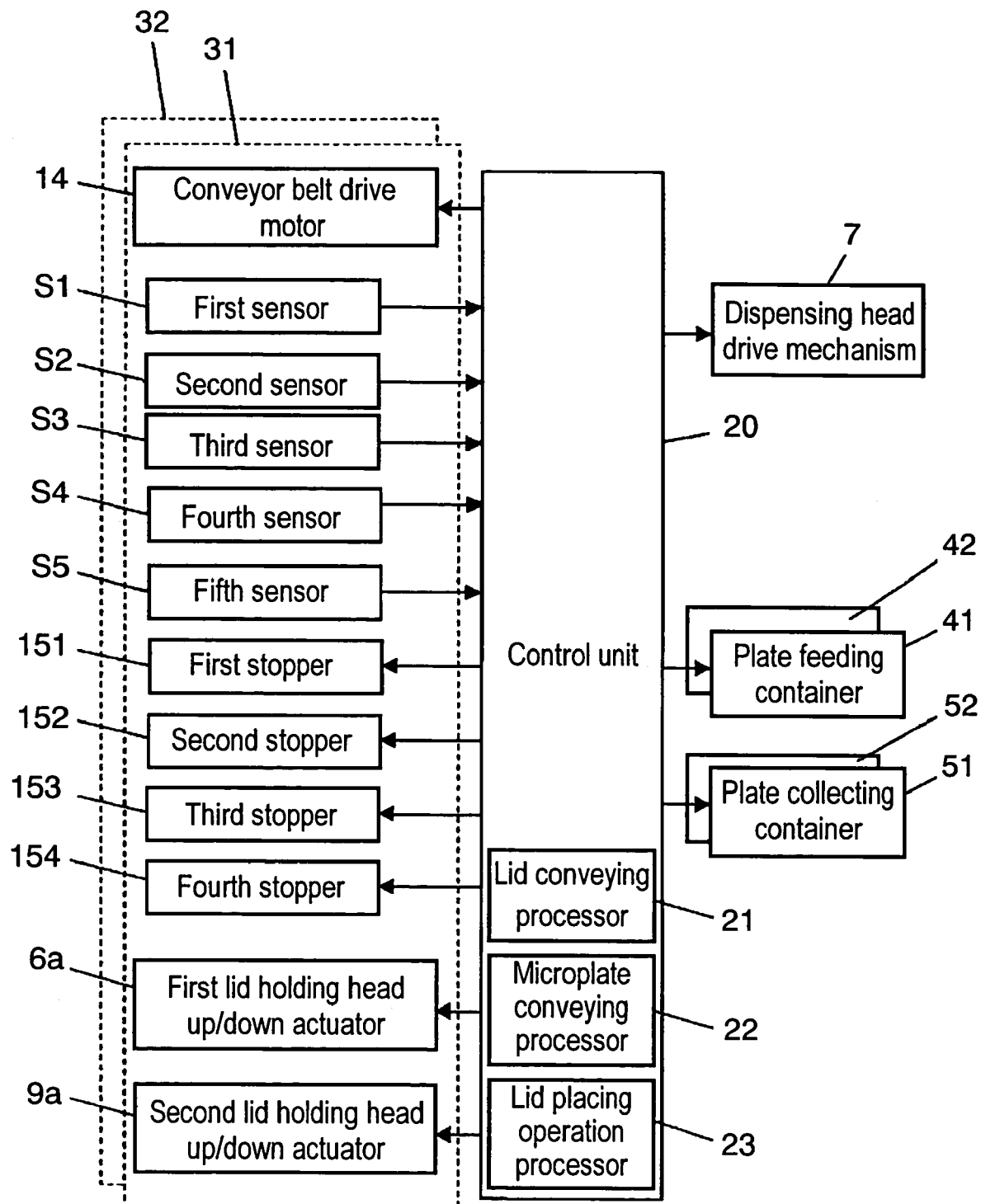

MICRO PLATE TREATING DEVICE AND MICRO PLATE CARRYING METHOD

RELATED APPLICATION

This application is the U.S. National Phase under 35 U.S.C. § 371 of International Application No. PCT/JP2005/006986, filed Apr. 5, 2005, which in turn claims the benefit of Japanese Application No. 2004-112975, filed Apr. 7, 2004, the disclosures of which Applications are incorporated by reference herein in their entirety.

TECHNICAL FIELD

The present invention relates to a microplate processing apparatus capable of performing given processes for microplates, and to a method of conveying microplates in the microplate processing apparatus.

BACKGROUND ART

In fields such as drug screening and biotechnology, biochemical reactions of substances and the like are tested. In the testing, a microplate is used as a container for containing drug solution and test substances with which cultivation and biochemical reactions are performed. The testing, usually performed systematically targeted for a large number of samples, processes a plurality of microplates in one testing for dispensing operation, componential analysis, and others.

Under the circumstances, as disclosed in Japanese Patent Unexamined Publication No. H11-223636, such a structure is known that is equipped with a feeding device for stocking a plurality of microplates; and a plate conveying mechanism for conveying microplates extracted from the feeding device, as a dedicated processing apparatus for performing the above-mentioned processes automatically. In this conventional example, microplates are individually contained in a storage rack provided with a plurality of plate placing positions; when feeding, microplates are extracted one by one by means of a plate conveying mechanism of a ceiling-travel robot type, and are transferred to the dispensing stage; and microplates having undergone the dispensing operation are returned to the storage rack.

A well for containing liquid, provided in a microplate, is open at its top surface. Therefore, when storing a microplate with liquid injected into its well, having undergone the dispensing operation, a lidded microplate may be used for isolating the injected liquid from the outside atmosphere, depending on a purpose of testing. In such a case, the lid needs to be attached and detached when performing processes such as dispensing operation for a microplate, and thus a microplate processing apparatus requires a function of attaching and detaching a microplate lid.

In the above-mentioned conventional example, for instance, the apparatus is equipped with a lid removing unit therein, and microplates individually move to the lid removing unit by the plate conveying mechanism every time before and after a dispensing operation is performed.

However, in the above-mentioned conventional example, only one set of lid removing unit is arranged at a fixed position. Consequently, a large number of microplates requiring being processed continuously make it difficult to attach and detach lids efficiently, which causes the entire processing to be inefficient.

SUMMARY OF THE INVENTION

A microplate processing apparatus according to the present invention has the following makeup.

A microplate processing apparatus that removes a microplate lid to perform a given process for the microplate, and attaches the lid after the process is completed, the apparatus equipped with a microplate conveying mechanism with a conveyor belt, for conveying the microplate in an order corresponding to a lid removing position, an intermediate position, and a lid attaching position, from upstream on a conveying path; a processing unit for performing a given process for the microplate at the intermediate position; a lid removing mechanism for removing the microplate lid at the lid removing position; a lid placing mechanism for placing the lid removed by the lid removing mechanism, on a downstream position from the microplate to which this lid was attached, on the conveying path of the microplate conveying mechanism; a lid attaching mechanism that picks up the lid conveyed from the lid removing position to the lid attaching position by the microplate conveying mechanism, by the microplate conveying mechanism, and attaches this lid to the microplate conveyed to the lid attaching position by the microplate conveying mechanism; a lid conveying processor for conveying the lid placed on this microplate conveying mechanism by the lid placing mechanism, from the lid removing position to the lid attaching position, by controlling the microplate conveying mechanism; and a microplate conveying processor that conveys the microplate with its lid removed by the lid removing mechanism, to the intermediate position, and conveys the microplate having undergone a given process by the processing unit, to the lid attaching position.

A method of conveying a microplate according to the present invention has the following steps.

A method of conveying a microplate in a microplate processing apparatus equipped with a microplate conveying mechanism with a conveyor belt, for conveying the microplate in an order corresponding to a lid removing position, an intermediate position, and a lid attaching position, from upstream on a conveying path, the method including a lid removing position conveying step for conveying the microplate with its lid attached, to the lid removing position, by the microplate conveying mechanism; a lid removing step for removing the microplate lid at the lid removing position; a lid placing step for placing the lid removed by the lid removing mechanism, on a downstream position from the microplate to which this lid was attached, on the conveying path of the microplate conveying mechanism; a lid conveying step for conveying the lid placed on this microplate conveying mechanism, from the lid removing position to the attaching position, by the microplate conveying mechanism; a lid picking up step for picking up the lid conveyed to the lid attaching position, from the microplate conveying mechanism, and for holding the lid; an intermediate position conveying step for conveying the microplate with its lid removed, by the microplate conveying mechanism; a lid attaching position conveying step for conveying the microplate having undergone a given process, to the lid attaching position, at the intermediate position; a lid attaching step for attaching the lid held in the lid picking up step, to the microplate conveyed to the lid attaching position; and a carrying out step for carrying out the microplate with its lid attached, from the lid attaching position, by the microplate conveying mechanism.

According to the present invention, the lid removed by the lid removing mechanism is placed on a downstream position from the microplate to which this lid was attached, on the conveying path of the microplate conveying mechanism, and conveyed to the lid attaching position in advance of the microplate. As a result that this lid is attached to the microplate conveyed to the lid attaching position after a given process is completed, attaching and detaching the lid to and from the microplate are performed efficiently.

BRIEF DESCRIPTION OF THE DRAWINGS

FIG. 3 is a block diagram illustrating the makeup of the control system for the microplate processing apparatus according to the embodiment.

DETAILED DESCRIPTION OF PREFERRED EMBODIMENT

Hereinafter, a description will be made for an embodiment of the present invention, using drawings.

Figure 1:
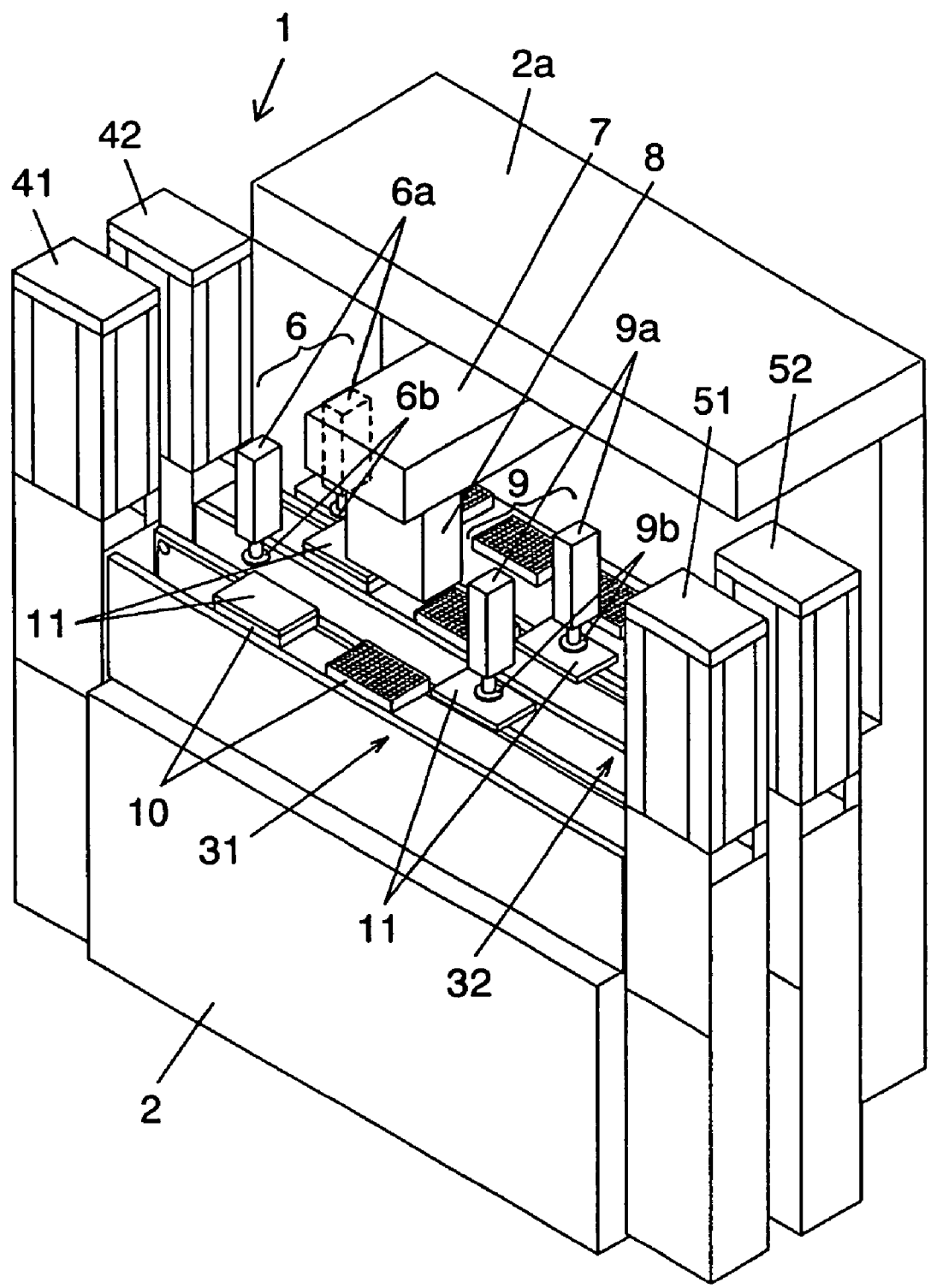
FIG. 1 is a perspective view of a microplate processing apparatus according to an embodiment of the present invention.
Figure 2:
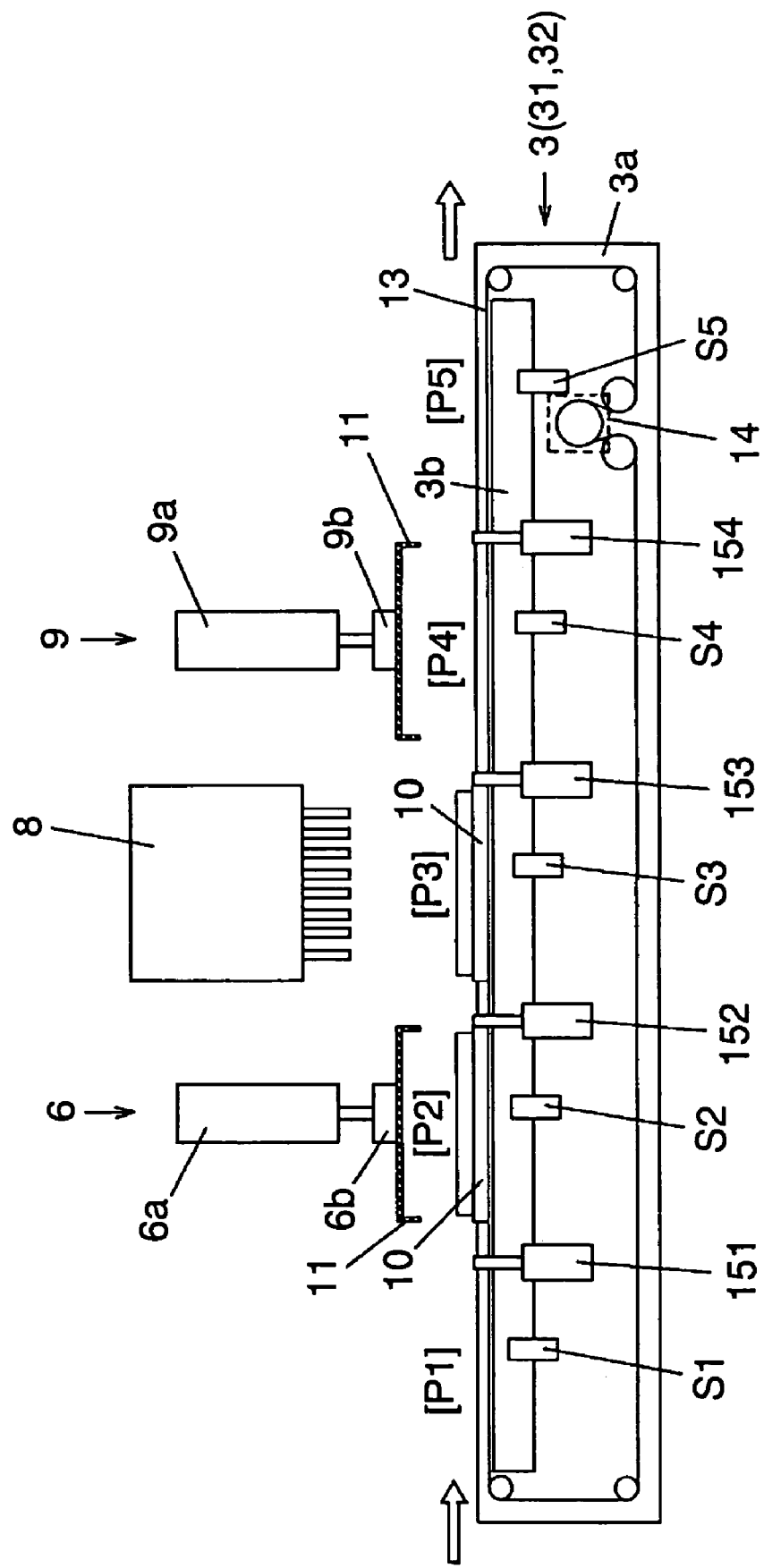
FIG. 2 is a front view of the microplate processing apparatus according to the embodiment.

FIG. 1 is a perspective view of a microplate processing apparatus according to an embodiment of the present invention; FIG. 2, front view of the microplate processing apparatus according to the embodiment; and FIG. 3, a block diagram illustrating the makeup of the control system for the microplate processing apparatus according to the embodiment. FIGS. 4A through 4D, FIGS. 5A through 5D, and FIGS. 6A through 6D are explanatory diagrams for the operation of the microplate processing apparatus according to the embodiment.

First, a description will be made for the entire structure of microplate processing apparatus 1, referring to FIG. 1.

Microplate processing apparatus 1, in biochemical testing and analysis such as in drug screening, has functions for removing the microplate lid to perform a given process for the microplate, and for attaching the lid after the process is completed. As shown in FIG. 1, in microplate processing apparatus 1, first microplate conveying mechanism 31 and second microplate conveying mechanism 32, both having the identical structure, are horizontally arranged on base 2 in parallel with each other; and dispensing head 8, movable owing to dispensing head drive mechanism 7, is allocated above these microplate conveying mechanisms. Further, first plate feeding container 41 and first plate collecting container 51 are arranged at both ends of first microplate conveying mechanism 31; second plate feeding container 42 and second plate collecting container 52, at both ends of second microplate conveying mechanism 32.

Microplates 10, test objects, are contained in first plate feeding container 41 and second plate feeding container 42. Microplates 10 fed one by one from first plate feeding container 41 and second plate feeding container 42, are conveyed downstream (to the right in FIG. 1) by means of first microplate conveying mechanism 31 and second microplate conveying mechanism 32, both with conveyor belts.

Then, a dispensing operation is performed for microplates 10 by dispensing head 8, on the conveying paths of first microplate conveying mechanism 31 and second microplate conveying mechanism 32. Microplates 10 having undergone the dispensing operation are conveyed downstream by first microplate conveying mechanism 31 and second microplate conveying mechanism 32, and collected to first plate collecting container 51 and second plate collecting container 52.

Microplate 10, a test object, is to be stocked with lid 11 attached to prevent foreign matter from being immixed. Lid 11 is attached and detached when dispensing operation is performed by dispensing head 8. Accordingly, microplate processing apparatus 1 is provided with lid removing mechanism 6 and lid attaching mechanism 9 for removing and attaching lid 11, upstream and downstream of dispensing head 8, respectively. Lid removing mechanism 6 and lid attaching mechanism 9 move up and down first lid holding head 6b and second lid holding head 9b, both capable of sucking and holding lid 11, by means of first lid holding head up/down actuator 6a and second lid holding head up/down actuator 9a, respectively.

Next, a description is made for the structures of first microplate conveying mechanism 31 and second microplate conveying mechanism 32, and their positional segments on the conveying path, referring to FIG. 2.

As shown in FIG. 2, first microplate conveying mechanism 31 and second microplate conveying mechanism 32 (hereinafter, collectively described as "microplate conveying mechanism 3" as long as discrimination is not required) have two pieces of guide plates 3a, arranged so as to face each other vertically in the conveying direction, as the frame of the conveyor body, and belt 13 driven by conveyor belt drive motor 14 travels on bearing plates 3b, horizontally provided in respective guide plates 3a.

The top surface of belt 13 born by bearing plate 3b for travel is a conveying path on which microplate 10 is placed and conveyed. The traveling direction of belt 13, namely the conveying direction, and the start/stop timing of conveying are arbitrarily controllable as required. The conveying path of microplate conveying mechanism 3 is segmented into the positions with their sizes in which microplate 10 can stay one each from upstream: first position [P1], second position [P2], third position [P3], fourth position [P4], and fifth position [P5].

First position [P1] is a receiving position for receiving microplate 10 fed from plate feeding containers 41 and 42 located upstream. The second position [P2] is a lid removing position for removing lid 11 from microplate 10 by lid removing mechanism 6. Meanwhile, fourth position [P4] is a lid attaching position for attaching lid 11 once removed at second position [P2], to microplate 10. Finally, third position [P3], located intermediately between second position [P2] and fourth position [P4], is an intermediate position for dispensing microplate 10 by dispensing head 8.

Therefore, in the above-mentioned makeup, dispensing head 8 is a processing unit for performing a given process for microplate 10 having been conveyed by microplate conveying mechanism 3, at the intermediate position. Lid removing mechanism 6 removes lid 11 of microplate 10 having been conveyed by microplate conveying mechanism 3, at second position [P2] (lid removing position). Further, lid attaching mechanism 9, to be hereinafter described, picks up lid 11 having been conveyed to fourth position [P4] in advance of microplate 10, after removed from microplate 10, and then attaches lid 11 to microplate 10 having been conveyed to fourth position [P4] later.

The respective positions are provided with sensors for detecting the presence of microplate 10 at each position: first sensor S1, second sensor S2, third sensor S3, fourth sensor S4, and fifth sensor S5. Meanwhile, first position [P1], second position [P2], third position [P3], and fourth position [P4] are provided with first stopper 151, second stopper 152, third stopper 153, and fourth stopper 154, respectively, for stopping microplate 10 at each position.

In other words, microplate conveying mechanism 3 is equipped with a plurality of stoppers for stopping microplate 10 at second position [P2], third position [P3], and fourth position [P4] (lid removing position, intermediate position, and lid attaching position, respectively).

Next, a description will be made for the makeup of the control system, referring to FIG. 3.

FIG. 3 specifically shows only first microplate conveying mechanism 31, out of the components of first microplate conveying mechanism 31 and second microplate conveying mechanism 32. Control unit 20 controls the operations of conveyor belt drive motor 14, first stopper 151, second stopper 152, third stopper 153, and fourth stopper 154, in the plate conveying operation by first microplate conveying mechanism 31 and second microplate conveying mechanism 32. At this moment, the detection results are referred to by first sensor S1, second sensor S2, third sensor S3, fourth sensor S4, and fifth sensor S5.

Control unit 20 further controls first lid holding head up/down actuator 6a and second lid holding head up/down actuator 9a, for the attaching and detaching operation of lid 11 performed during the plate conveying operation. Control unit 20 controls the moving operation of dispensing head 8 when dispensing microplate 10, by controlling dispensing head drive mechanism 7. Control unit 20 controls the feeding and collecting operations of microplate 10, by controlling first plate feeding container 41, second plate feeding container 42, first plate collecting container 51, and second plate collecting container 52.

Next, a description is made for the processing functions of lid conveying processor 21, microplate conveying processor 22, and lid placing operation processor 23, shown in FIG. 3.

These processing functions are implemented as a result that control unit 20 controls the aforementioned respective elements based on the processing program stored in a storage device (illustration omitted). With these functions, attaching and detaching operations of lid 11 are performed in the process of conveying microplate 10 by microplate conveying mechanism 3.

First, a description is made for lid placing operation processor 23.

In the process of a plate by microplate processing apparatus 1, after lid 11 is removed at second position [P2] by lid removing mechanism 6, from microplate 10 that has been fed, with lid 11 attached, microplate 10 is conveyed to third position [P3], and a given process is performed for this microplate 10. Then, lid 11 is to be attached to microplate 10 conveyed to fourth position [P4] after the process is completed, by means of lid attaching mechanism 9. Here, the correspondence between microplate 10 and lid 11 is not in random order, but lid 11 that was attached when fed is to be always attached to its original microplate 10, in order to prevent foreign matter from being immixed into liquid contained in microplate 10.

Accordingly, in microplate processing apparatus 1 according to this embodiment, lid 11 removed at second position [P2] is conveyed to fourth position [P4] in advance of microplate 10, and is preliminarily held in lid attaching mechanism 9. Then, the lid 11 is to be attached to microplate 10, when microplate 10 after the process is completed at third position [P3], is conveyed to fourth position [P4].

In order to implement these lid attaching and detaching operations by the same microplate conveying mechanism 3, as described later, microplate conveying mechanism 3 is controlled by lid placing operation processor 23 so that the conveying direction of microplate 10 with lid 11 removed is reversed, to be conveyed upstream. This is to cause an evacuating operation that evacuates relevant microplate 10 from second position [P2] (lid removing position), and a lid placing operation that places lid 11 on second position [P2] where microplate 10 has been evacuated, by controlling lid removing mechanism 6.

In other words, an operational process is performed by a lid placing mechanism to be hereinafter described, the process that places lid 11 removed by lid removing mechanism 6, on a downstream position from microplate 10 to which this lid 11 was attached, on the conveying path of microplate conveying mechanism 3. In this way, after removed lid 11 is positioned downstream of the body of microplate 10, microplate 10 and lid 11 are conveyed by microplate conveying mechanism 3. As a result, microplate 10 fed together with lid 11 attached can be separately conveyed, that is, microplate 10 to third position [P3], and lid 11 to fourth position [P4].

Therefore, in this embodiment, lid placing operation processor 23 is the aforementioned lid placing mechanism. Lid attaching mechanism 9 picks up lid 11 conveyed from second position [P2] to fourth position [P4] by microplate conveying mechanism 3, from microplate conveying mechanism 3, and then attaches this lid 11 to microplate 10 conveyed to fourth position [P4] by microplate conveying mechanism 3.

In the above-mentioned lid attaching and detaching operations, lid 11 and microplate 10 need to be conveyed to a specified position at a specified timing. What perform this conveying process are lid conveying processor 21 and microplate conveying processor 22. Lid conveying processor 21 conveys lid 11 placed on microplate conveying mechanism 3 by the aforementioned lid placing mechanism, from second position [P2] to fourth position [P4], by controlling microplate conveying mechanism 3. Meanwhile, microplate conveying processor 22 conveys microplate 10 with lid 11 removed, to third position [P3] (intermediate position), by controlling microplate conveying mechanism 3, and conveys microplate 10 having undergone a dispensing process by dispensing head 8 at third position [P3], to fourth position [P4].

Microplate processing apparatus 1 is composed as mentioned above. A description will be hereinafter made for a method of conveying microplates in microplate processing apparatus 1, referring to FIGS. 4A through 6D.

Figure 4A:
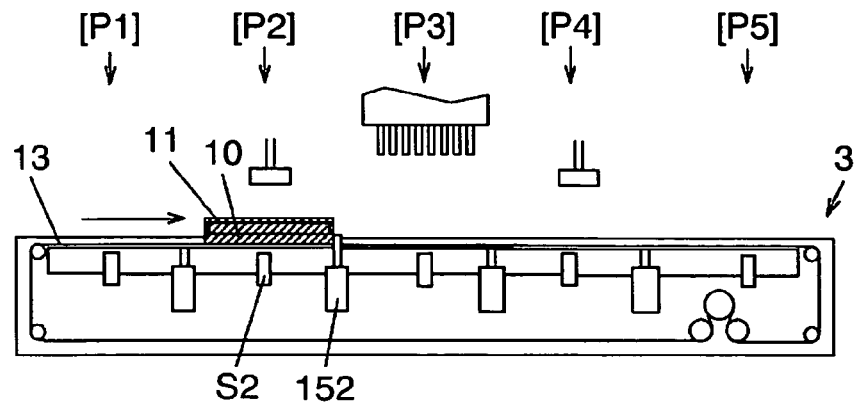
FIG. 4A is an explanatory diagram for the operation of the microplate processing apparatus according to the embodiment.

When starting the process in microplate processing apparatus 1, microplate 10 fed from first plate feeding container 41 or second plate feeding container 42, is placed on first position [P1] with lid 11 attached, as shown in FIG. 4A, and conveyed to second position [P2] as a result that belt 13 travels downstream.

Figure 4B:
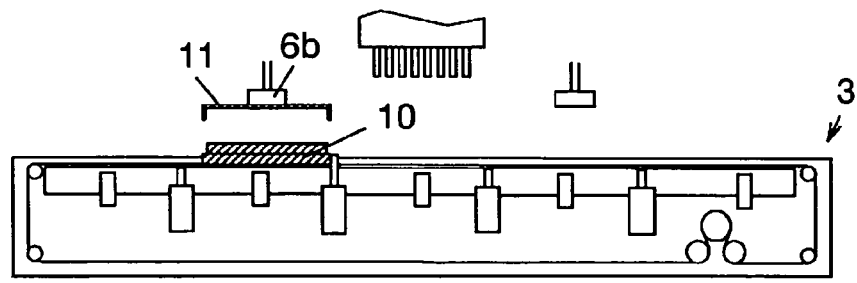
FIG. 4B is an explanatory diagram for the operation of the microplate processing apparatus according to the embodiment.

Then, microplate 10 is stopped at second position [P2] by second stopper 152 that is preliminarily located at the elevated position. In other words, microplate 10 with lid 11 attached is conveyed to second position [P2] (lid removing position), by microplate conveying mechanism 3 (lid removing position conveying step). Here, when a given standby time elapses after second sensor S2 detects microplate 10, first lid holding head 6b moves down, to remove lid 11 from microplate 10, as shown in FIG. 4B. That is, lid 11 is removed from microplate 10 at second position [P2] (lid removing step).

Figure 4C:
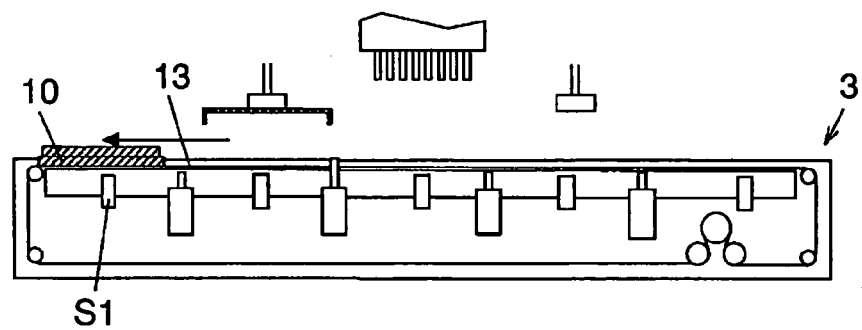
FIG. 4C is an explanatory diagram for the operation of the microplate processing apparatus according to the embodiment.
Figure 4D:
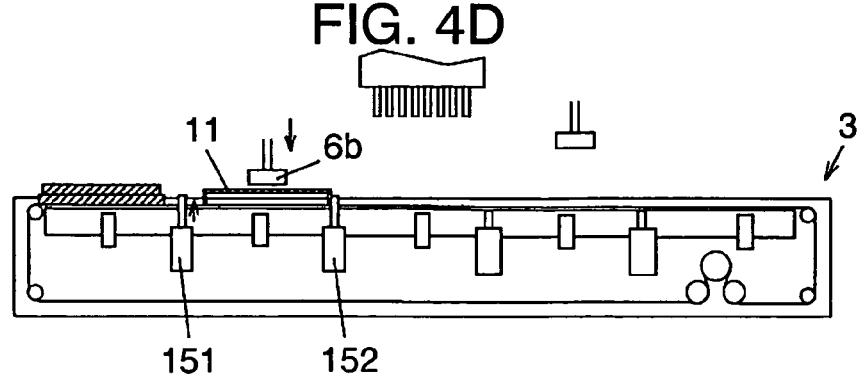
FIG. 4D is an explanatory diagram for the operation of the microplate processing apparatus according to the embodiment.

After then, as shown in FIG. 4C, the traveling direction of belt 13 is reversed to invert the conveying direction, moving microplate 10 to first position [P1], to be evacuated from second position [P2]. In other words, microplate 10 with lid 11 removed is conveyed upstream after the lid is removed, and is evacuated from second position [P2] (microplate evacuating step). Subsequently, as shown in FIG. 4D, lid 11 is placed on second position [P2] that is empty as a result that relevant microplate 10 has been evacuated after the microplate evacuating step (lid placing step).

As a result that the microplate evacuating step and lid placing step shown here are executed, the lid placing step is executed that places lid 11 removed in the lid removing step, on a downstream position from microplate 10 with this lid 11 having been attached, on the conveying path of microplate conveying mechanism 3. In other words, the lid placing step includes the microplate evacuating step and lid placing step.

Figure 5A:
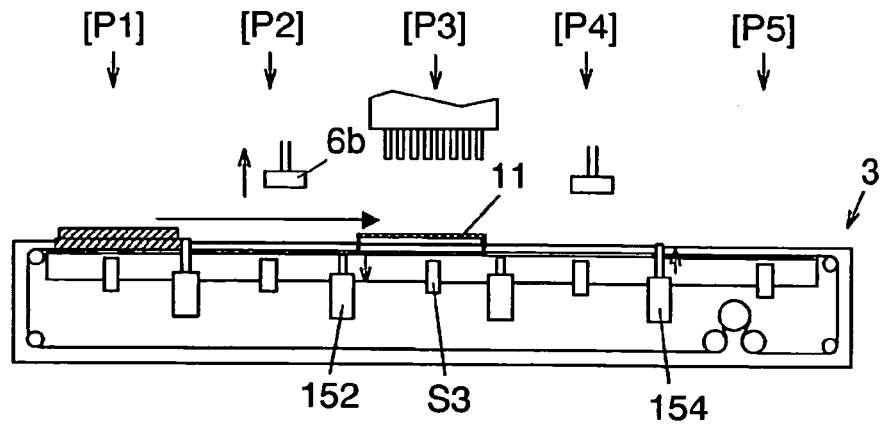
FIG. 5A is an explanatory diagram for the operation of the microplate processing apparatus according to the embodiment.
Figure 5B:
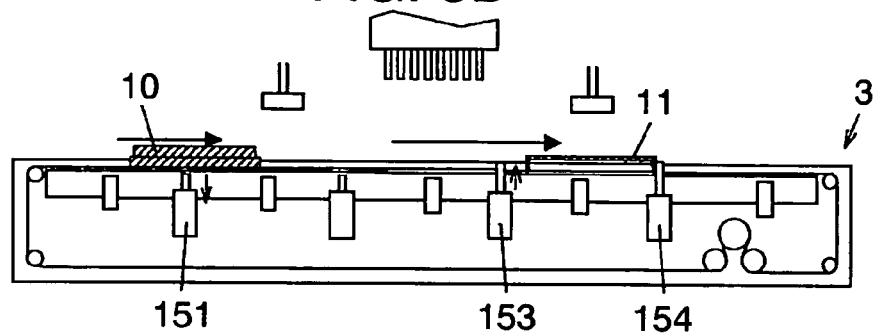
FIG. 5B is an explanatory diagram for the operation of the microplate processing apparatus according to the embodiment.

After then, microplate 10 and lid 11 are conveyed. More specifically, as shown in FIG. 5A, second stopper 152 is released after first lid holding head 6b is elevated, to convey lid 11 from second position [P2] to third position [P3], while elevating fourth stopper 154. When third sensor S3 detects lid 11, first stopper 151 is released to convey microplate 10 to second position [P2], as shown in FIG. 5B.

Figure 5C:
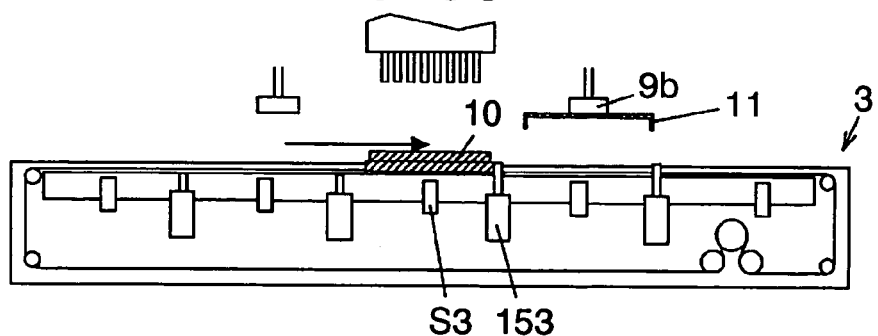
FIG. 5C is an explanatory diagram for the operation of the microplate processing apparatus according to the embodiment.
Figure 5D:
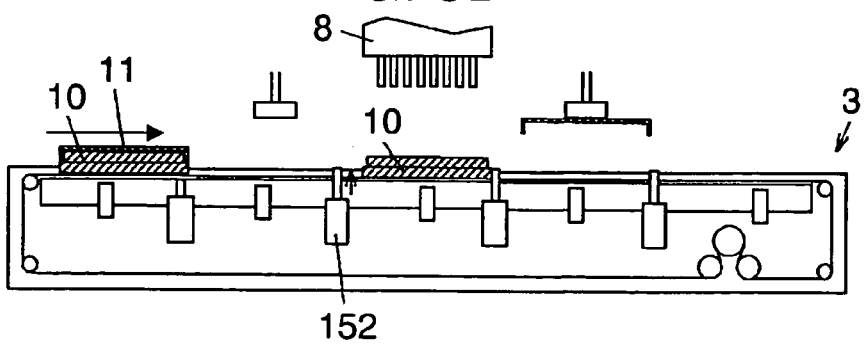
FIG. 5D is an explanatory diagram for the operation of the microplate processing apparatus according to the embodiment.

At this moment, lid 11 reaches fourth position [P4], to be stopped by fourth stopper 154. When a given standby time elapses after fourth sensor S4 detects that this lid 11 has reached, third stopper 153 is elevated. This causes, as shown in FIG. 5C, microplate 10 to stop at third position [P3]. Concurrently, second lid holding head 9b moves down to pick up and retain lid 11 at fourth position [P4].

In other words, the following steps are executed here: a lid conveying step for conveying lid 11 placed on this microplate conveying mechanism 3, from second position [P2] to fourth position [P4], by microplate conveying mechanism 3; a lid picking up step for picking up lid 11 conveyed to fourth position [P4], from microplate conveying mechanism 3, to be held; and an intermediate position conveying step for conveying microplate 10 with lid 11 removed, to third position [P3] (intermediate position), by microplate conveying mechanism 3.

Then in third position [P3], when a given standby time elapses after microplate 10 is detected by third sensor S3, a dispensing process targeted for microplate 10 by dispensing head 8 is started. At this moment, first position [P1] is fed with new microplate 10 with lid 11 attached, and second stopper 152 is elevated. After that, when a given time elapses after microplate 10 is detected by second sensor S2, travel of belt 13 is stopped, and the completion of the dispensing process at third position [P3] is waited. At this moment, lid 11 is not removed from microplate 10, but the lid-attached state is held, at second position [P2].

Figure 6A:
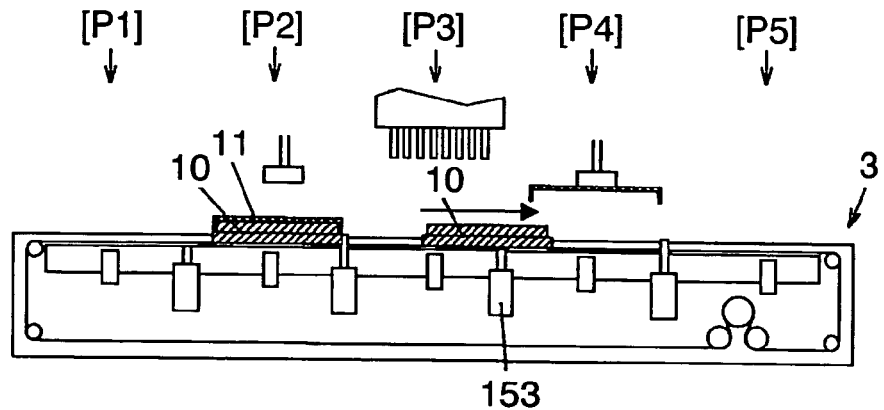
FIG. 6A is an explanatory diagram for the operation of the microplate processing apparatus according to the embodiment.
Figure 6B:
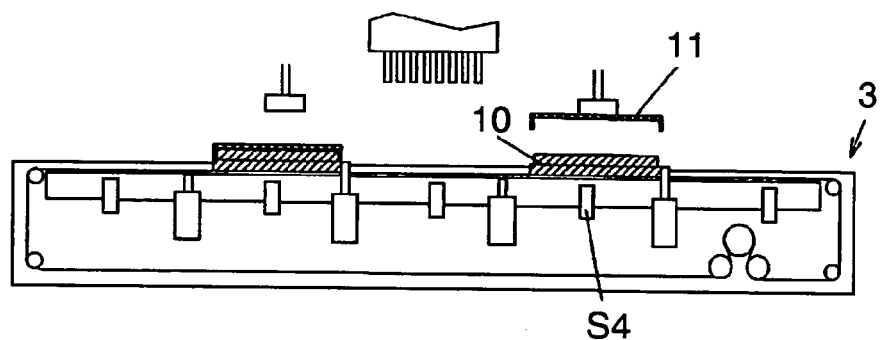
FIG. 6B is an explanatory diagram for the operation of the microplate processing apparatus according to the embodiment.

After that, when the dispensing process by dispensing head 8 is completed at third position [P3], microplate 10 having undergone a dispensing operation is conveyed to fourth position [P4], as shown in FIGS. 6A and 6B. In other words, microplate 10 having undergone a given process at the intermediate position is conveyed to fourth position [P4] (lid attaching position) (lid attaching position conveying step). Then in fourth position [P4], when a given time elapses after microplate 10 is detected by fourth sensor S4, lid 11 held in second lid holding head 9b is attached to microplate 10.

Figure 6C:
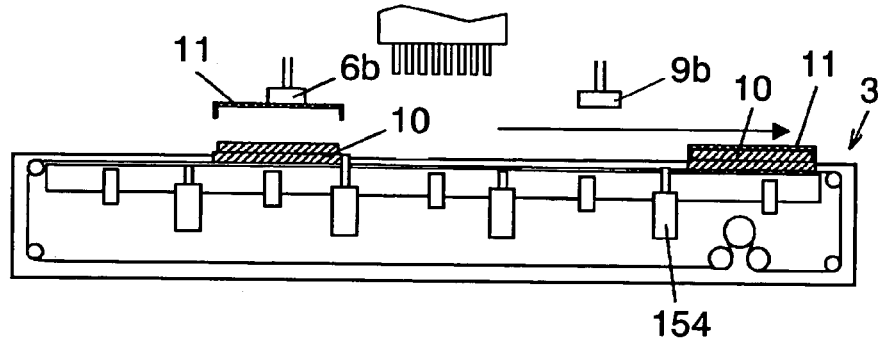
FIG. 6C is an explanatory diagram for the operation of the microplate processing apparatus according to the embodiment.

This causes lid 11 removed from microplate 10 in the lid removing step, to be attached to the original microplate 10 to which relevant lid 11 was attached, in the lid attaching step. After that, when second lid holding head 9b is elevated, fourth stopper 154 is released to convey microplate 10 to fifth position [P5], as shown in FIG. 6C. Concurrently, in second position [P2], first lid holding head 6b is moved up and down to remove lid 11 from microplate 10.

Figure 6D:
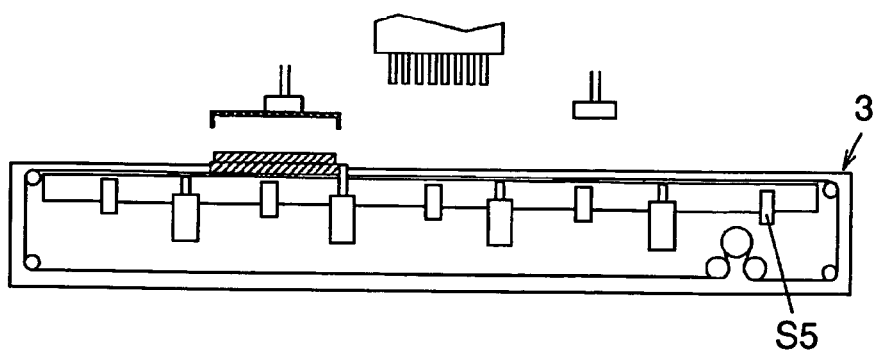
FIG. 6D is an explanatory diagram for the operation of the microplate processing apparatus according to the embodiment.

Subsequently, when a given time elapses after fifth sensor S5 detects that microplate 10 has passed through, it is judged that carrying out of microplate 10 that has turned into a lid-attached state after the dispensing process, from microplate conveying mechanism 3, has been completed, as shown in FIG. 6D. Then, in FIG. 4C again, the same operation is iteratively executed from then on, targeted for microplate 10 positioned at second position [P2].

As mentioned above, as a result that lid 11 removed by lid removing mechanism 6 is placed on a downstream position from the original microplate 10, on the conveying path of microplate conveying mechanism 3, to be conveyed to the lid attaching position in advance of this microplate 10, lid 11 can be attached to microplate 10 having undergone a process. This makeup allows lid 11 to be attached and detached efficiently in a microplate processing apparatus that performs processes while continuously conveying a large number of microplates 10 by a single microplate conveying mechanism.

INDUSTRIAL APPLICABILITY

A microplate processing apparatus according to the present invention is effective in that the lid of a microplate is efficiently attached to and detached from the microplate, for continuous processes targeted for a microplate requiring a lid to be attached.

The invention claimed is:

1. A method of conveying a microplate in a microplate processing apparatus equipped with a conveyor belt, adapted to convey the microplate and lid to a plurality of positions including, as situated in upstream to downstream order, a lid removing position, an intermediate position, and a lid attaching position, the method comprising:
a lid removing position conveying step for conveying the microplate with the lid thereof attached by the conveyor belt, to the lid removing position;

a lid removing step for removing the lid of the microplate at the lid removing position;

a lid placing step for placing the lid removed in the lid removing step, on a downstream position from the microplate with the lid having been attached, on the conveyor belt;

a lid conveying step for conveying the lid placed on the conveyor belt by the conveyor belt, from the lid removing position to the lid attaching position;

a lid picking up step for picking up the lid conveyed to the lid attaching position, from the conveyor belt, and for holding the lid;

an intermediate position conveying step for conveying the microplate with the lid removed by the conveyor belt, to the intermediate position;

a lid attaching position conveying step for conveying the microplate having undergone a given process at the intermediate position, to the lid attaching position;

a lid attaching step for attaching the lid held in the lid picking up step, to a microplate conveyed to the lid attaching position; and a carrying out step for carrying out the microplate with the lid attached by the conveyor belt, from the lid attaching position, wherein the lid placing step includes:

a microplate evacuating step for conveying the microplate with the lid thereof removed, upstream, and for evacuating the microplate from the lid removing position, after the lid removing step; and a lid positioning step for placing the lid on the removing position that is empty as a result that the relevant microplate is evacuated, after the microplate evacuating step.

2. The method of conveying the microplate of claim 1, wherein the lid removed from the microplate in the lid removing step, is attached to an original microplate with the relevant lid having been attached, in the lid attaching step.

* * * * *